United States Patent [19]
Akers et al.

[11] Patent Number: 4,612,916
[45] Date of Patent: Sep. 23, 1986

[54] METHOD FOR TREATING CASUALTIES IN A CONTAMINATED AREA

[75] Inventors: Charles K. Akers; Roland J. Pilié, both of Williamsville, N.Y.

[73] Assignee: Calspan Corporation, Buffalo, N.Y.

[21] Appl. No.: 634,243

[22] Filed: Jul. 25, 1984

Related U.S. Application Data

[62] Division of Ser. No. 501,733, Jun. 6, 1983, Pat. No. 4,485,490.

[51] Int. Cl.$^4$ .................. A41D 13/00; A61F 13/00
[52] U.S. Cl. ........................... 128/1 R; 128/132 R; 2/2
[58] Field of Search ............. 128/1 R, 132 D, 132 R; 2/2, 69, DIG. 7; 24/205, 384

[56] References Cited

U.S. PATENT DOCUMENTS

| 2,664,890 | 1/1954 | Wallace | 128/1 R |
| 2,741,410 | 4/1956 | La Violette | 223/111 |
| 3,670,218 | 6/1972 | Borendgord | 128/1 R |
| 3,907,389 | 9/1975 | Cox et al. | 128/1 R X |
| 4,214,317 | 7/1980 | Kelly | 2/2 |
| 4,275,719 | 6/1981 | Mayer | 128/1 R X |
| 4,304,224 | 12/1981 | Fortney | 2/DIG. 7 |
| 4,485,489 | 12/1984 | Pilié et al. | 128/1 R |
| 4,485,490 | 12/1984 | Abers et al. | 128/2 |

Primary Examiner—Edward M. Coven
Attorney, Agent, or Firm—Biebel, French & Nauman

[57] ABSTRACT

Treatment of casualties enclosed in garments which protect them from a contaminated environment comprises attaching treatment apparatus containing uncontaminated treatment space to the protective garment and then effecting communication between the treatment space and the interior of the garment. The treatment apparatus comprises a generally rectangular enclosure having an access opening on one side with fastener means provided for closing the access opening. The fastener means are compatible with at least a portion of the fastener means for the protective garment to permit coupling the enclosure to the garment and then communicating the treatment space with the interior of the garment. The treatment apparatus includes an observation window opposite to the fastener device and sealed gloved openings to permit manipulation by treating personnel within the intercoupled treatment space and the interior of the garment. Provision is made in the treatment apparatus for the storage of various instruments, equipment and medication for use in treating casualties in the field.

2 Claims, 11 Drawing Figures

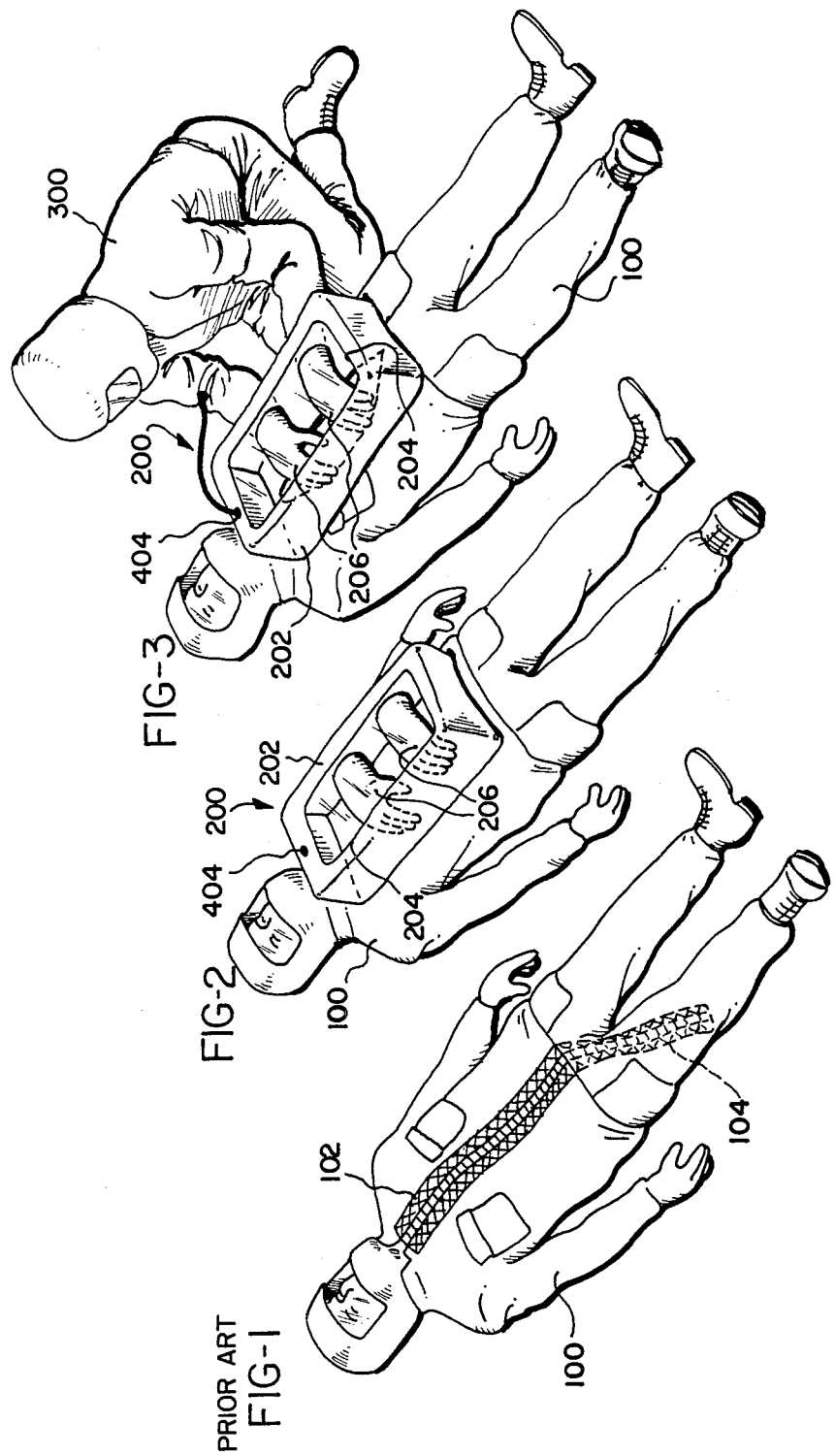

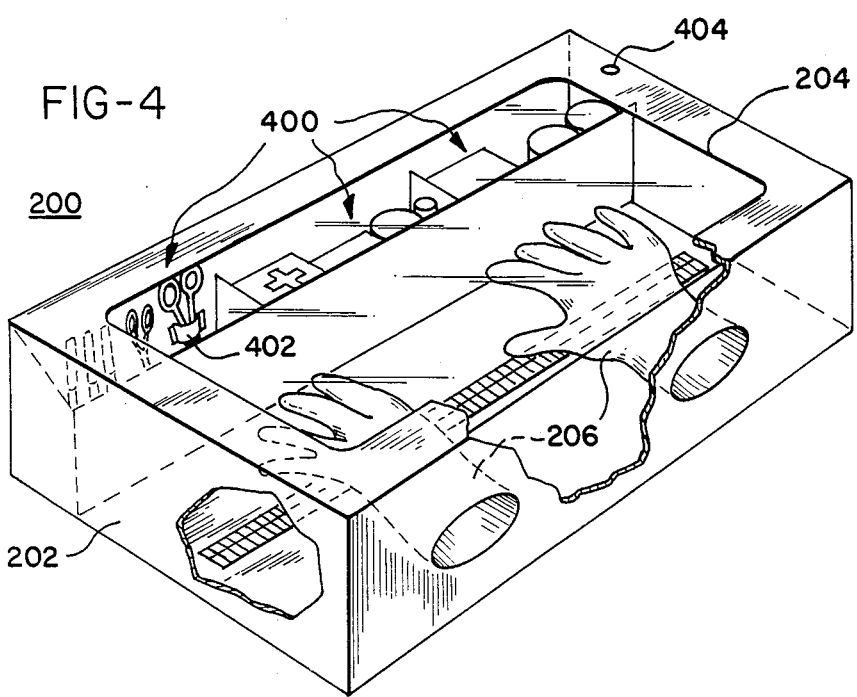

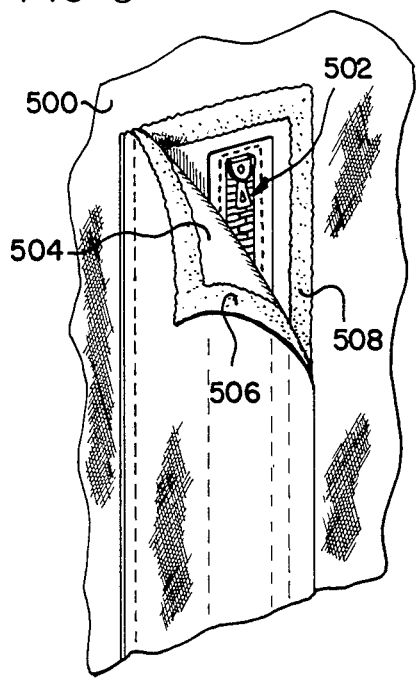
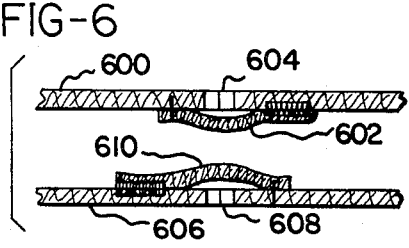
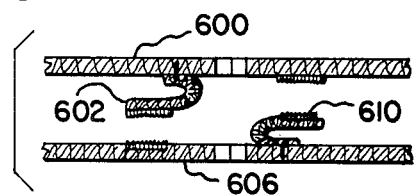
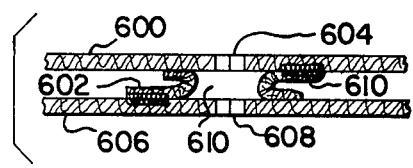
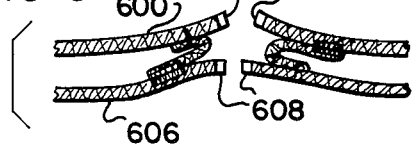
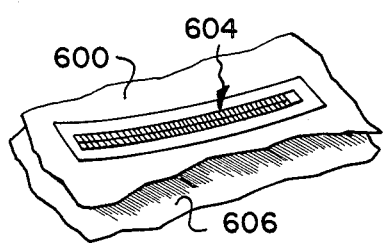
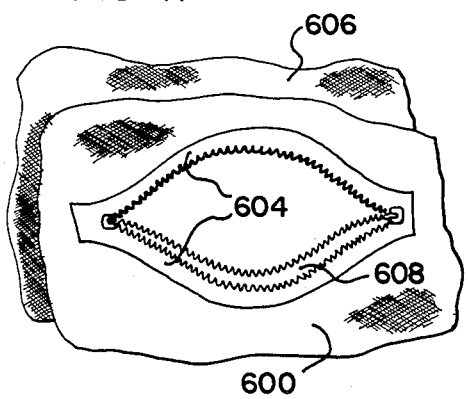

METHOD FOR TREATING CASUALTIES IN A CONTAMINATED AREA

This is a division of application Ser. No. 501,733, filed June 6, 1983, now U.S. Pat. No. 4,485,490.

BACKGROUND OF THE INVENTION

This invention relates generally to individuals who are encapsulated in protective garments and more particularly to the treatment of such individuals while in a chemically contaminated environment when such individuals become casualties Within the scope of personnel protection against a chemically contaminated environment such as would result from chemical warfare, the protection of individuals is a high priority. Effective protection of individuals is provided by a protective garment which includes a sealed face mask and respiration system to filter and purify air drawn into the garment. However, persons in such garments are subject to physiological and thermal stresses, chemical injuries due for example to exceeding the filter capacity of their respiration system as well as wounds inflicted by more conventional weaponry.

Rapid entrance and egress of personnel protected by such garments into and out of protective shelters as well as the treatment of casualties within a chemically contaminated environment by moving them into larger protective shelters was addressed by U.S. patent application Ser. No. 390,100 filed June 21, 1982, and assigned to the same assignee as the present application. However, moving many casualties to a protective shelter and removing the persons from the protective garments into the shelter by use of a specially designed ambulance, may not always be practical. Ambulances obviously cannot be provided in numbers sufficient to care for potentially numerous casualties which may occur in a contaminated area, for example, as the result of chemical/conventional warfare. Since presently it is not otherwise possible to gain access to a casualty in a chemically contaminated area to observe life signs, and to administer necessary fist aid in the field without contaminating the casualty, the need exists for a method and apparatus for field treatment of casualties in a chemically contaminated area.

SUMMARY OF THE INVENTION

In accordance with the present invention, treatment apparatus for a casualty within a contaminated environment attaches to first fastener means of a protective garment which encloses the casualty. The treatment apparatus comprises a container providing uncontaminated treatment space therewithin. An access opening in the container permits communication between the treatment space and the interior of the protective garment. Second fastener means are provided on the container for closing the access opening, and the second fastener means is compatible with at least a portion of the first fastener means of the protective garment to permit coupling the container to the garment and adding the treatment space to the protected interior of the garment. Handling means, such as one or two integral gloves, are included in the container so the hands of treating personnel can manipulate within the treatment space, and a window in the container provides for observing treatment activities within the treatment space and the interior of the garment.

Preferably, the container comprises a generally rectangular compartment with the access opening and second fastener means being placed on a side opposite to the window, and the handling means positioned on a third side of the compartment. Storage is provided within the treatment space for receiving diagnostic instruments, treatment instruments and medication for use in treating a casualty via the uncontaminated treatment space.

The first fastener on the protective garments runs substantially the entire length of the casualty's torso and can run beyond those dimensions particularly for rapid ingress and egress from the garment. The second fastener extends substantially the entire length of the compartment, which is preferably sized to approximately correspond in length to a casualty's torso. The second fastener is adapted to mate with at least a portion of the first fastener to form a closed passage between the fasteners through which the treatment space and the interior of the garment are in closed communication with each other.

Also disclosed is a method for treating casualties in a contaminated area by means of an uncontaminated treatment space confined within an enclosure having a sealed observation panel using the aforementioned apparatus. The casualties enclosed within protective garments are treated by a method comprising the steps of: placing the enclosure against the protective garment such that the fasteners on each align with one another; operating the fasteners to interconnect the enclosure with the protective garment and to communicate the treatment space with the interior of the garment, while keeping intact the protection of the surrounding area; utilizing the handling means to contact the casualty while protected within the protective garment; and observing the operations performed within the treatment space and the communicating interior of the protective garment through the observation panel.

It is, therefore, an object of the present invention to provide a method and apparatus for treating casualties in a contaminated area by providing an uncontaminated treatment space which is coupled to a protective garment such that the treatment space can be placed in closed communication with the interior of the garment; and to provide such a method and apparatus for treating casualties in a contaminated area wherein an uncontaminated treatment space containing appropriate diagnostic instruments, treatment instruments and medication are provided therewithin for treatment of casualties once the treatment space is sealingly coupled to a protective garment enclosing the casualty.

Other objects and advantages of the invention will be apparent from the following description, the accompanying drawings and the appended claims.

BRIEF DESCRIPTION OF THE DRAWINGS

FIG. 1 is a perspective view of a casualty enclosed in a protective garment positioned for treatment with the apparatus in accordance with the present invention.

FIG. 2 is a perspective view of the casualty of FIG. 1 with the treatment apparatus in accordance with the present invention connected to the protective garment.

FIG. 3 is a perspective view of a person utilizing the apparatus in accordance with the present invention to treat a casualty.

FIG. 4 is a perspective view of the treatment apparatus in accordance with the present invention.

FIG. 5 is a perspective view of one end of an illustrative fastener for use in the present invention with the corner of a secondary fastener flap opened to expose the operating end of a closed primary fastener.

FIGS. 6-9 are diagrammatic partial cross-section views showing the sequence of operating the primary and secondary fasteners shown in FIG. 5.

FIGS. 10 and 11 are perspective views of two short fasteners as shown in FIG. 5 with the secondary fasteners connected one to the other and with the primary fasteners closed and opened, respectively.

DETAILED DESCRIPTION OF THE INVENTION

FIGS. 1-3 illustrate the method of treating a casualty in a contaminated area with the treatment apparatus in accordance with the present invention. FIG. 1 shows a casualty enclosed in a protective garment 100 including hand, feet and head covers. Such protective garments are known in the art and, hence, will not be described further herein. The protective garment 100 includes fastener means 102 an illustrative embodiment of which will be described hereinafter. The fastener means 102 preferably will extend at least the entire length of the casualty's torso and may include an extension 104 down one of the garment's legs to permit cooperation with the entrance and egress system for protective shelters as disclosed in said U.S. application Ser. No. 390,100 cited above.

The treatment apparatus in accordance with the present invention comprises container means preferably comprising a rectangular compartment 202 which includes an access opening closed by fastener means which cooperate with the fastener means 102 of the protective garment. The treatment apparatus 200 is shown in more detail in FIG. 4 and the operation of illustrative fasteners for use in the present invention are fully disclosed hereinafter with reference to FIGS. 5-11. The compartment 202 is attached to the fastener means 102 as shown in FIG. 2 so that window means 204 positioned opposite to the fastener means in the compartment 202 face upwardly. Handling means comprise two sealed gloved openings 206 in the preferred embodiment, which gloved openings are placed in a third side of the compartment 202.

The sealed gloved openings extend into the interior of the compartment which comprises uncontaminated treatment space wherein diagnostic instruments, treatment instruments and/or medication, as more fully shown in FIG. 4, are stored for use by treating personnel.

In FIG. 3, a person 300, typically a medic, who attached the compartment 202 to the garment 100 of the casualty has opened the fastener means to permit communication between the treatment space and the inside of the protective garment so that the vital signs of the casualty may be monitored and the casualty treated. As shown in FIG. 3, the treating person 300 has inserted his hands into the sealed gloved openings 206, and the treatment space as well as the interior of the protective garment 100 of the casualty is maintained in an uncontaminated condition.

The treatment apparatus in accordance with the present invention is shown in more detail in the perspective view of FIG. 4. In addition to the structure previously described, various compartments 400 are provided for the storage of diagnostic and treatment instruments as well as necessary medication. The compartments 400 may include various loops 402 for supporting scissors or other instruments and may extend around the ends of the rectangular compartment 202 or alternately be limited to the ends of the compartment 202. Bandages, pads, tape and other standard first aid treating equipment may be included within the treatment apparatus. An electronic stethoscope may also be included and coupled to a receiving unit in the protective garment of the treating person 300 via a sealed connector 404. Since one of the major problems with protective garments is the possibility of heat prostration, the treatment apparatus typically would also include endothermic reaction bags to be applied to the casualty of heat prostration to cool and restore the casualty to mobility so that more permanent treatment facilities could be reached.

FIGS. 5-11 show an illustrative embodiment of the fastener means incorporated into the access opening of the compartment 202 as well as the protective garment 100. These fasteners are the same as described in greater detail in said U.S. application Ser. No. 390,100; however, it should be understood that other fastener means may be employed. Another embodiment of suitable fastener means is disclosed in U.S. application Ser. No. 452,658, filed Dec. 23, 1982, entitled "Interchange Mechanism for Multiple Fasteners", and assigned to the same assignee as the present application.

FIG. 5 shows a portion of the underside of the compartment 202 which comprises a sheet 500 of flexible material in which an elongated slit-like opening is formed which opening is closed by a primary fastener 502 illustrated schematically as a zipper which may have tabs on both sides for operation from either side. Fastened to the enclosure bottom sheet 500 along one side of the primary fastener 502 is a flap 504 which is sealed to the compartment bottom sheet 500 along a line which also defines the hinge of the flap 504.

The flap 504 is sufficiently large to extend completely over and beyond the primary fastener 502. Around the outer edge of the inner face of the flap 504 is one-half of a secondary fastener 506. The other half of the secondary fastener 508 is firmly affixed to the enclosure bottom sheet 500 to align with the outer edge of the flap 504 when the flap is closed over the primary fastener 502. The secondary fastener may be a hook/latch type of fastener such as disclosed in U.S. Pat. No. 2,717,437 issued to Velcro S. A., which fastener per se is well known. The flap 504 together with the secondary fastener 506, 508 can be closed to cover the slit-like opening in the enclosure bottom sheet 500 and totally surround the primary fastener 502. Accordingly, if the otherwise sealed compartment 202 is exposed to a contaminated environment, the flap 504 covers and protects the primary fastener 502 and the surrounding region beneath the flap.

In accordance with the present invention, one fastener device is provided on the protective garment and a complementary fastener device is provided on the bottom of the treatment apparatus. FIGS. 6-9 illustrate the sequence of mating the treatment compartment 202 to a protective garment 100 so that an uncontaminated treatment space is available for ministering to a casualty in a contaminated area. In FIG. 6, a bottom sheet 600 of a treatment compartment is shown with its sealing flap 602 or secondary fastener means closed to surround its similarly closed primary fastener means 604. The complementary fastener device on the front panel 606 of a protective garment having its primary fastener means 608 closed and covered by its closed flap 610 or secondary fastener means is brought into intermating relationship with the bottom sheet 600 as shown.

In FIG. 7, the flaps 602 and 610 are opened. The intermating relationship between the two fastener means is illustrated in FIG. 7 by the two panels being arranged such that the hook material on the flap is aligned with the latch material on the surface of the opposite fastener section. The fasteners are pressed together as shown in FIG. 8 to provide an elongated and totally surrounded protective area 610, as shown in FIG. 8, with the primary fastener means still closed. In the event that the few moments of opening the two flaps 602 and 610 might allow some contaminate to enter the region between the flaps and around the primary fastener means, a decontaminate agent can be introduced by, for example, having a suitable decontaminate available within the protective area 610 in a frangible capsule or the like should this precaution be necessary.

With the treatment compartment 202 connected to the protective garment 100 by way of the flaps 602 and 610, the primary fastener means 604 and 608 can be opened as shown in FIG. 9. Opening the primary fastener means 604 and 608 results in a passage or opening communicating the uncontaminated treatment space within the treatment compartment 202 with the interior of the protective garment 100.

FIG. 10 is a perspective view illustrating the attachment of the bottom sheet 600 to the protective garment 100 as viewed from inside the treatment compartment 202 with the primary fastener means 604 and 608 closed. FIG. 11 is a perspective view from inside the treatment compartment 202 showing the communication between the treatment space within the compartment 202 and the interior of the protective garment 100 with the primary fastener means 604 and 608 opened and the opening flexed apart.

In view of the teachings of the present application, various modifications and alternate embodiments will be apparent to those skilled in the art. For example, it will be recognized that a variety of sizes and shapes of the treatment apparatus can be provided as well as various arrangements for storing instruments and medication within the uncontaminated treatment compartment.

Thus, while the method herein described and the form of apparatus for carrying the method into effect constitute a preferred embodiment of this invention, it is to be understood that the invention is not limited to this precise method and form of apparatus and that changes may be made in either without departing from the scope of the invention which is defined in the appended claims.

What is claimed is:

1. A method for treating casualties in a contaminated area by means of an uncontaminated treatment space confined within an enclosure having a sealed observation panel, sealed handling means for permitting manipulation within said treatment space and an access opening closed by first fastener means, said casualties being enclosed within protective garments including second fastener means for permitting access into the interior of said garments, said method comprising the steps of:
   placing said enclosure against a protective garment such that said first and second fastener means align with one another;
   operating said first and second fastener means to interconnect said enclosure with said protective garment and to communicate said treatment space with the interior of said garment;
   utilizing said handling means to contact said casualty while enclosed within said protective garment; and
   observing the operations performed within said treatment space and the communicating interior of said protective garment through said observation panel.

2. The method of claim 1 wherein said first fastener means comprises first primary fastener means attached to said enclosure for repeated opening and closing of said access opening and first secondary fastener means surrounding and covering said first primary fastener means, and said second fastener means comprises second primary fastener means attached to said garments and adapted for repeated opening and closing thereof and second secondary fastener means on the exterior of said garments surrounding and covering said second primary fastener means, said first and second secondary fastener means being cooperatively connectable one to another, the step of operating said first and second fastener means comprises the steps of:
   connecting said first secondary fastener means to said second secondary fastener means of one of said garments to form a passage between said enclosure and said one garment, said passage extending between said first primary fastener means and said second primary fastener means;
   opening said first primary fastener means to communicate said treatment space with said passage; and
   opening said second primary fastener means to communicate said passage with the interior of said one garment.

* * * * *